United States Patent [19]

Harms et al.

[11] 4,258,712

[45] Mar. 31, 1981

[54] EQUIPMENT SETS HAVING A PILOT LIQUID CONTROLLED PRIMARY TUBE VALVE FOR THE SEQUENTIAL ADMINISTRATION OF MEDICAL LIQUIDS AT DUAL FLOW RATES

[75] Inventors: Jack L. Harms, Mundelein; Joseph N. Genese, Waukegan; Andrew J. Muetterties, Lake, all of Ill.

[73] Assignee: Abbott Laboratories, North Chicago, Ill.

[21] Appl. No.: 16,268

[22] Filed: Feb. 28, 1979

[51] Int. Cl.³ .......................................... A61M 05/14
[52] U.S. Cl. ............................ 128/214 G; 128/227; 137/113; 222/145
[58] Field of Search ......... 128/214 R, 214 C, 214 G, 128/214.2, 227, 274; 222/129.2, 145; 137/112–114, 859

[56] References Cited

U.S. PATENT DOCUMENTS

| 788,176 | 4/1905 | Traves | 128/227 |
| 3,633,605 | 1/1972 | Smith | 137/113 |
| 3,886,937 | 6/1975 | Bobo et al. | 128/214 G |
| 4,105,029 | 8/1978 | Virag | 128/214 G |
| 4,116,646 | 9/1978 | Edwards | 128/214 R X |

FOREIGN PATENT DOCUMENTS

| 1099294 | 2/1961 | Fed. Rep. of Germany | 137/113 |
| 1375258 | 9/1964 | France | 137/589 |

Primary Examiner—Dalton L. Truluck
Attorney, Agent, or Firm—Robert L. Niblack; Aaron L. Hardt; Robert S. Beiser

[57] ABSTRACT

Equipment sets for the sequential administration of medical liquids wherein a primary liquid can be administered at a flow rate independent of the flow rate of a secondary liquid, and including a barrier substantially impervious to air to prevent the inadvertent administration of air when the secondary liquid is depleted. The equipment sets of this invention have a primary tube valve controlled by pilot liquid diverted from the secondary liquid flow path.

30 Claims, 3 Drawing Figures

EQUIPMENT SETS HAVING A PILOT LIQUID CONTROLLED PRIMARY TUBE VALVE FOR THE SEQUENTIAL ADMINISTRATION OF MEDICAL LIQUIDS AT DUAL FLOW RATES

BACKGROUND OF THE INVENTION

The present invention relates to systems and equipment sets for the administration of medical liquids to a patient, and more particularly, to systems and equipment sets for the sequential administration of a plurality of medical liquids employing a primary tube valve controlled by a pilot liquid diverted from the secondary liquid flow path.

The parenteral administration of medical liquids to patients is a long established practice. Liquids including amino acids, blood, dextrose, electrolytes, and saline are commonly administered to patients over prolonged periods of time. Generally, these liquids are administered from a glass bottle or plastic bag suspended above the patient and containing 250–2,000 ml. of the liquid. Such prolonged infusions commonly are administered at a flow rate of 10–150 ml./hr.

Frequently, the patient must receive an additive or secondary liquid while the prolonged infusion is being administered. Preferably, this secondary liquid should be administered through the same hypodermic needle to avoid unnecessary pain and trauma to the patient of additional venipunctures. To avoid dilution and incompatability problems, it is also preferable that the flow of the primary liquid employed in the prolonged infusion be temporarily interrupted, the secondary liquid administered and the flow of the primary liquid resumed. Generally, the secondary liquid will be administered at a flow rate of 50–250 ml./hr.

Abbott Laboratories, North Chicago, I.L. manufactures a y-type set for the sequential administration of primary and secondary liquids. These VENOSET piggyback sets allow the prolonged infusion of a primary liquid to be temporarily halted by means of a backcheck valve in the primary liquid flow path to administer a secondary liquid without the need for a new venipuncture. Then, when the secondary liquid has been depleted, the backcheck valve automatically opens to resume flow of the primary liquid. An important characteristic of this system is that the secondary liquid container must be suspended at a higher height than the primary liquid container to establish the liquid pressure differential that closes the backcheck valve in the primary liquid flow path.

A similar system is disclosed in U.S. Pat. No. 3,886,937 granted June 3, 1975 to D. Bobo, et al., assigned to American Hospital Supply Corp., and entitled "Medical Administration Set for Dispensing Plural Medical Liquids". Another similar system is disclosed in U.S. Pat. No. 4,105,029 granted Aug. 8, 1978 to R. Virag, assigned to Baxter Travenol and entitled "Intravenous Solution Set Having An Air Access Site and Constricted Inner Diameter Portion".

An inherent disadvantage of the above-mentioned prior art medical liquid administration systems is that they each resume the flow of primary liquid at the rate the secondary liquid had been flowing. Because the preferred flow rate of the secondary liquid is generally greater than the preferred flow rate of the primary liquid, when the primary liquid resumes flow at that rate, the patient can be administered an excessive amount of primary liquid, unless the flow rate of the primary liquid is adjusted to the preferred primary liquid flow rate soon after the flow of primary liquid resumes.

A remedy to the above-described disadvantage would appear to be provided by simply incorporating flow control devices into both the primary and secondary liquid flow paths. However, while this remedy does provide dual flow rates for the primary and secondary liquids, it is unacceptable. That is, because the common tube of the y-set must be able to accommodate both flow rates, when the primary liquid is flowing at a slower rate than the secondary liquid was, there will be an unfilled volume or void in the common tube. To fill that void, air will be drawn into the common tube from the depleted secondary container. That air will then be driven into the patient by the weight of the primary liquid, thereby causing a serious embolism and perhaps, the patient's death.

Accordingly, it will be apparent that an efficacious system for the sequential administration of medical liquids at dual flow rates would be advantageous to the medical profession.

SUMMARY OF THE INVENTION

The primary object of the present invention, therefore, is to provide an equipment set for the sequential administration of medical liquids at dual flow rates that will not draw air from the secondary container when the secondary liquid has been depleted.

In accordance with this and other objects, there is provided by the present invention an equipment set for the sequential administration of medical liquids to a patient including a primary tube, a secondary tube, and a common tube all connected in fluid communication to form a primary liquid flow path and a secondary liquid flow path. The primary liquid flow path includes the primary and common tube, while the secondary liquid flow path includes the secondary and common tubes.

The primary tube includes a primary valve which allows primary liquid to flow from a primary liquid container whenever the height of primary liquid is greater than or equal to the height of the secondary liquid in the system. The primary valve prevents primary liquid from flowing out of the primary container whenever the height of the primary liquid is less than the height of the secondary liquid in the system by means of a pilot liquid diverted from the secondary liquid flow path. Preferably, the primary valve can be a flexible diaphragm valve. Further, if so desired, the primary tube can include a second primary valve, e.g., a backcheck valve, on the proximal side of the first primary valve.

To establish the dual flow rates of the primary and secondary liquids, a secondary flow control means in the secondary liquid flow path for adjusting the flow rate of the secondary liquid and a primary flow control means on the primary tube for adjusting the flow rate of the primary liquid to a rate greater than, less than, or equal to the flow rate of the secondary liquid are provided. An air barrier in the secondary liquid flow path that is substantially impervious to air is provided to insure that no air is drawn from the secondary container when the secondary liquid is depleted.

BRIEF DESCRIPTION OF THE DRAWING

Other objects and attendant advantages will become obvious to those skilled in the art by reading the follow

DETAILED DESCRIPTION OF THE INVENTION

Figure 1:
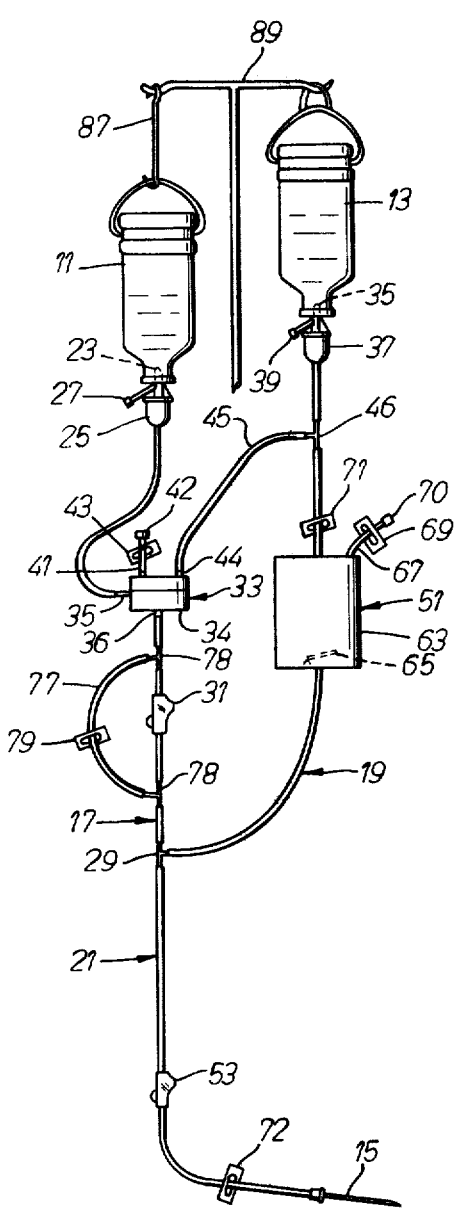
- FIG. 1 is a front elevational view of one embodiment of the efficacious equipment sets for the sequential administration of medical liquids at dual flow rates contemplated by this invention.

Referring to the drawing, there is shown in FIG. 1, the basic elements of the equipment sets for the sequential administration of medical liquids at dual flow rates contemplated by this invention.

FIG. 1 depicts a primary liquid container 11 that contains a primary medical liquid to be administered to a patient for a prolonged period of time. FIG. 1 also depicts a secondary liquid container 13 that contains a secondary medical liquid to be administered to the patient for a relatively short period of time, during which time the administration of the primary liquid will be temporarily interrupted. Containers 11 and 13 can be glass bottles, plastic flexible bags, or any other suitable container.

Primary container 11 and secondary container 13 are connected in fluid communication to a conventional hypodermic needle 15 through a primary tube 17, a secondary tube 19, and a common tube 21. Thus, the primary liquid flow path from primary container 11 to needle 15 comprises primary tube 17 and common tube 21. Likewise, the secondary liquid flow path from secondary container 13 to needle 15 comprises secondary tube 19 and common tube 21.

The distal end of primary tube 17 is in fluid communication with primary container 11, preferably by means of a piercing pin 23 inserted into a puncturable closure of container 11. Piercing pin 23 can have an integral drip chamber 25, and when container 11 is a glass bottle, as shown in the set of FIG. 1, an integral, filtered air vent 27. Such piercing pins, drip chambers and air vents are well known in the medical practice and need not be more fully explained here.

Figure 3:
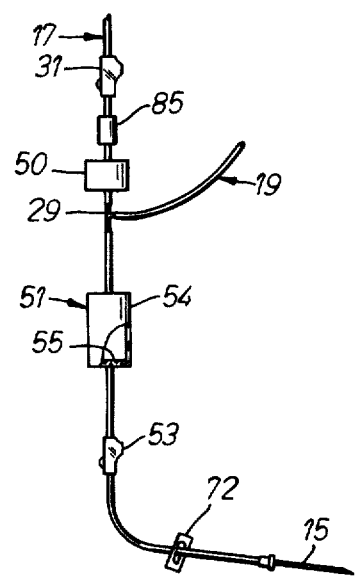
FIG. 3 is a front elevational view of a portion of the set of FIG. 1 including additional alternative elements therein.

The proximal end of primary tube 17 is joined in fluid communication to the distal end of common tube 21, preferably by a y-tube 29, it being understood that the primary, secondary and common legs of y-tube 29 constitute a portion of the primary, secondary and common tubes 17, 19 and 21, respectively. Primary tube 17 has a primary flow control 31 intermediate its ends for independently adjusting the rate flow of the primary liquid through the primary liquid flow path. Preferably, as shown in FIGS. 1 and 3, primary flow control 31 can be a roller clamp. However, it can be any other adjustable device that will reliably maintain a desired primary liquid flow rate.

Primary tube 17 includes a primary valve 33, preferably, between its distal end and primary flow control 31. Primary valve 33 allows primary liquid to flow from primary container 11 whenever the height of the primary liquid is greater than or equal to the height of the secondary liquid in the system of FIG. 1. Further, primary valve 33 is controlled by pilot liquid diverted from the secondary liquid flow path to prevent the flow of primary liquid from primary container 11 whenever the height of the primary liquid is less than the height of the secondary liquid in the system.

Figure 2:
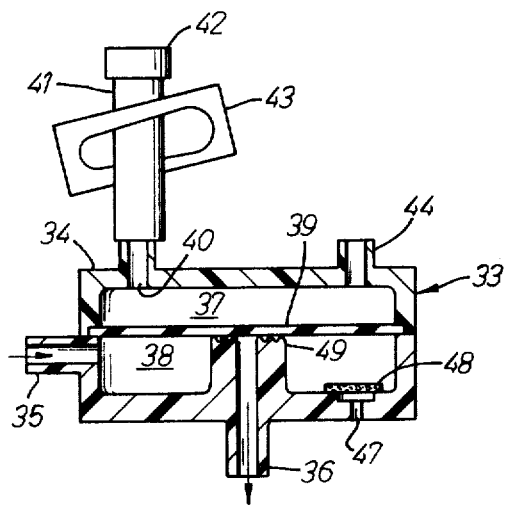
FIG. 2 is a front elevational view in cross-section of a preferred flexible diaphragm valve embodying the pilot liquid controlled primary valve depicted in FIG. 1.

Primary valve 33 has a housing 34 having an inlet 35 and outlet 36 in fluid communication with primary tube 17 and constitutes a portion of it. As best seen in FIG. 2, a preferred embodiment of primary valve 33 is a flexible diaphragm valve in which housing 34 is divided into two chambers 37, 38 by an air and liquid impermeable, flexible diaphragm 39. Diaphragm 39 is, preferably, made of an elastomeric material, such as natural or silicone rubber. Diaphragm 39 can also be made of thermoplastic materials, such as polyethylene. As shown in FIG. 2, diaphragm 39 can be captured between halves of housing 34, or alternatively, it can be insert-molded into a single piece housing.

Chamber 37 has an air vent 40 which includes a tube 41 having a filtered end 42 and a slide clamp 43 which can be slid to open vent 40 to the passage of air and closed to prevent the passage of fluid. Chamber 37 has a port 44 through housing 34 and connected in fluid communication to secondary tube 19 by a pilot tube 45, preferably, by means of a y-tube 46. Optionally, pilot tube 45 can be provided with a slide clamp intermediate its ends, in which instance, slide clamp 43 on tube 41 can be eliminated.

Chamber 38 has an air vent 47 through which ambient air can enter and exit. Vent 47 is covered by a hydrophobic membrane 48 which is permeable by air, but not liquids.

As seen in FIG. 2, outlet 36, preferably, extends into chamber 38 a substantial distance and its inner end 49 forms a seat on which flexible diaphragm 39 can seat to close outlet 36 to air and liquid. Preferably, inner end 49 of outlet 36 is provided a plurality of protrusions to form a plurality of seats on which flexible diaphragm 39 can seat. Preferably, the plurality of protrusions are formed by a plurality of concentric rings of unequal heights, the height of the respective rings decreasing in a direction from the perimeter of inner end 49 towards its center.

Alternatively, air vent 47 can be provided a filtered tube and slide clamp as shown for air vent 40 of chamber 37. Likewise, air vent 40 can be covered by a hydrophobic filter as shown for air vent 47, when pilot tube 45 is provided a slide clamp.

Preferably, flexible membrane 39 will have sufficient weight and elastic memory to maintain outlet 36 normally closed. However, flexible membrane 39 can be made so that outlet 36 is normally opened and only closed by the weight of a pilot liquid. Further, while housing 34 has been shown in its horizontal position in FIGS. 1 and 2, it will be readily apparent that it can be vertically and otherwise positioned and still function properly.

As shown in FIG. 3, primary tube 17 can be provided a redundant or second primary valve 50. Second primary valve 50 will open and close under the same conditions required to either open or close primary valve 33.

While second primary valve 50 has been shown in the set of FIG. 3 as being spaced from the proximal end of primary tube 17, it will be readily apparent that second primary valve 50 can be incorporated into the primary leg of y-tube 29, if so desired. For example, primary valve 50 can be a conventional, one-way, backcheck valve mounted within the primary leg of y-tube 29.

The distal end of secondary tube 19 is in fluid communication with secondary container 13, preferably, by means of a piercing pin 35 inserted into a puncturable closure of container 13. Piercing pin 35 can have an integral drip chamber 37, and when container 13 is a glass bottle, as shown in FIG. 1, an integral, filtered air vent 39. The proximal end of secondary tube 19 is joined in fluid communication to the distal end of common tube 21, preferably, by a y-tube 29.

An air barrier 51 and secondary flow control 53 are located in the secondary liquid flow path. Preferably, as shown in FIGS. 1 and 3, secondary flow control 53 can be a roller clamp. However, it can be any other adjustable device that can reliably maintain a desired secondary liquid flow rate.

As shown in FIG. 1, air barrier 51 is located in secondary tube 19, which is its preferred location. However, as shown in FIG. 3, air barrier 51 can be located in common tube 21, if so desired. Likewise, for increased reliability of the system, a plurality of air barriers 51 can be located in either the seconday tube 19, common tube 21, or both. Further, while air barrier 51 is shown spaced from the proximal end of secondary tube 19 and distal end of common tube 21, it will be readily apparent that air barrier 51 can be incorporated into the secondary or common tube leg of y-tube 29.

As shown in the set of FIG. 3, air barrier 51 comprises a housing 54 having an inlet and outlet in fluid communication with common tube 19 and constitutes a portion of it. The outlet from housing 54 is covered by a hydrophilic membrane filter 55 which is impermeable to air when wet. The hydrophilic filter can be formed from materials such as a cellulose acetate material produced by the Millipore Filter Corporation of Bedford, Massachusetts or the Sartorius-Membranfilter GmbH of Weender Landstr, West Germany.

The air barrier 51 shown in the set of FIG. 1 comprises a housing 63 that has an inlet and outlet in fluid communication with secondary tube 19 and constitutes a portion of it. The outlet from housing 63 has a float valve 65 which floats away from the outlet when liquid is present in housing 63, but seats or closes over the outlet when no liquid is present. It will be apparent to those skilled in the art that numerous other conventional mechanical valves can be employed to perform the function of float valve 65, so long as the valve forms a barrier impermeable by air when no liquid is present in the housing 63.

Housing 63 of the set shown in FIG. 1 also includes an air vent tube 67 having a slide clamp 69 and a filtered opening 70. Alternatively, opening 70 can be filtered by a hydrophobic membrane filter which is permeable by air, but not liquids. The hydrophobic filters used in this invention can be formed of polyfluorotetraethylene, hexafluoropropylene/tetrafluoroethylene copolymer, or other suitable materials. One such filter is made of Gelman ANH-450 material made by Gelman Instruments of Ann Arbor, Mich. When such a hydrophobic filter is used, slide clamp 69 can be eliminated.

The sets shown in FIGS. 1 and 3 include a slide clamp 71 near the distal end of secondary tube 19 and a slide clamp 72 near the proximal end of common tube 21.

In the set of FIG. 1, primary tube 17 includes a priming tube 77 having a slide clamp 79 that controls the flow of primary liquid through priming tube 77. Priming tube 77 is joined in parallel to the main branch of primary tube 17 by y-tubes 78 located on each side of primary control means 31. As will be more fully explained in the following paragraphs, priming tube 17 allows primary control means 31 to remain at its preferred adjustment while the set of FIG. 1 is being primed or backprimed at a higher flow rate.

Primary flow control 31 is shown on the distal side of second primary valve 50 in FIG. 3. It has been found that for pressure differentials of the magnitude occuring in the system of this invention, location of primary flow control 31 on the proximal side of second primary valve 50, for most of the preferred settings of primary flow control 31, results in a greater pressure being exerted on second primary valve 50 by primary liquid than by secondary liquid. As a result, second primary valve 50 remains open, as if the height of primary liquid were greater than or equal to the height of secondary liquid in the system.

Surprisingly, it has been found that when primary flow control 31 is located on the distal side of second primary valve 50, as shown in FIG. 3, certain embodiments of primary valve 50 might not remain closed as expected whenever the height of primary liquid is less than the height of secondary liquid in the system. This unexpected opening results from the reaction force on second primary valve 50 caused by primary liquid that cannot flow upwardly past primary flow control 31 when second primary valve 50 initially closes. This reaction force reopens valve 50 and keeps it open.

It has been found that this unexpected opening of second primary valve 50 can be obviated by the inclusion in primary tube 17 of a chamber 85 for a compressible mass. As shown in FIG. 3, chamber 85 is located between primary flow control 31 and second primary valve 50 and provides a cushion or spring for relieving pressures on the distal side of second primary valve 50 whenever valve 50 closes in response to the height of primary liquid being less than the height of secondary liquid in the system. Although second primary valve 50 and chamber 85 are shown as separate units in FIG. 3, it will be apparent that they can be combined into one unit, if so desired.

As shown in the set of FIG. 3, chamber 85 has a housing with an inlet and outlet in fluid communication with primary tube 17. However, it is contemplated that chamber 85 can have only one opening in communication with primary tube 17. That is, chamber 85 may have a single opening transverse to the normal flow of liquid through primary tube 17 so that primary liquid only flows in or out of its single opening when reverse flow pressures exist on the distal side of second primary valve 50.

Generally, the compressible mass of chamber 85 will be air and its housing will be a rigid opaque plastic. However, it is contemplated that the compressible mass of chamber 85 can be a sponge or other flexible solid materials, as well. Further, the housing of chamber 85 can be a flexible material which is compressible by the primary liquid to expand chamber 85, if so desired.

For simplicity, the equipment sets of this invention have been depicted and described as integral units in FIGS. 1 and 3. It is apparent, however, that the sets can be manufactured and assembled in subsets of the entire set and that each subset will accordingly be provided such resealable closures, piercing means, adapters etc. as are necessary to permit their easy assemblage into the complete set at an appropriate time. It will also be apparent that many of the several components of the sets of FIGS. 1 and 3 can be interchanged or combined in combinations other than those specifically depicted, especially air barriers 51.

OPERATION OF THE SYSTEM

As depicted in FIG. 1, primary container 11 is suspended in space at a height above the patient by means of a hook 87 and stand 89. It will be apparent that other means for suspending the containers of this invention are well known.

To insure that all the air that might be forced into the patient has been removed from the set, the set is initially primed by first closing all slide clamps 43, 69, 71, 72 and 79, if present. Piercing pin 23 is then inserted into the resealable closure of primary container 11. Primary flow control 31 and secondary flow control 53 are fully opened. Slide clamp 72 is opened to allow primary liquid to flow through the primary liquid flow path and force all the air therefrom that might be forced into the patient. If chamber 85 is present in primary tube 17, a substantial volume of air will remain therein. If air barrier 51 is present in common tube 21, it will be inverted so that primary liquid must fill all of housing 54 before it enters the outlet. Slide clamp 72 is then closed.

Clamp 69 on air vent 67 of air barrier 51 is then opened to allow primary liquid to flow into, or back-prime, secondary flow path 19 and force all the air from air barrier 51. Slide clamp 70 is then closed. Alternatively, if the set is fully assembled, slide clamp 71 can be opened to allow primary liquid to force air out of the entire secondary tube 19. Slide clamp 71 is then closed.

During the initial priming of secondary tube 19, it is advantageous to hold secondary tube 19 at a height well below primary container 11. When secondary tube 19 has been primed, it is secured in a convenient place until its subsequent use.

Common tube 21, which, preferably, has an adapter at its proximal end open to the flow of liquid therefrom, is next connected to needle 15, which will generally have been already inserted into a vein of the patient. Slide clamp 72 will then be opened to allow primary liquid to flow through the primary liquid flow path to the patient's vein. Primary flow control 31 is then adjusted to a setting that will provide the desired flow rate for a prolonged infusion of primary liquid into the patient, generally 10–150 ml./hr. As is well known in the medical practice, that flow rate can be visually observed by viewing and counting drops passing through the primary drip chamber 25.

Subsequently, when it is desired to administer a secondary liquid to a patient, piercing pin 35 of secondary tube 19 is inserted into the resealable closure of secondary container 13. If any portion of secondary tube 19 has not already been primed, it can now be primed with secondary container 13 held at a height well below primary container 11, secondary tube slide clamp 71 opened, common tube slide clamp 72 closed and priming tube slide clamp 79, if present, opened.

Primary liquid then is allowed to flow into, or back-prime, secondary tube 19 until all the air that can be forced into the patient has been expelled from secondary tube 19. If present, priming tube 77 allows the primary liquid to bybass the primary flow control and flow into secondary tube 19 at the fastest possible rate. Slide clamp 43 on primary valve 33 is then opened.

Secondary container 13 is then suspended in space from stand 89 at a height substantially greater than the height of primary container 11, thereby immediately causing primary valve 33 and second primary valve 50, if present, to close. Priming tube slide clamp 79, if present, is then closed and common tube slide clamp 72 opened. Secondary flow control 53 is then adjusted to a desired flow rate, typically 50–250 ml./hr., for the secondary liquid, which will then flow until the secondary container 13 is depleted. It will be apparent that the initial liquid flowing from secondary tube 19 will be the primary liquid with which it was primed.

When secondary container 13 was initially suspended, secondary liquid was immediately diverted from the secondary liquid flow path into chamber 37 of primary valve 39 through pilot tube 45. It will be readily apparent that the diverted secondary liquid does not pass through valve 33 to the patient, but rather remains in chamber 37 as a pilot liquid through which the pressure of secondary liquid in secondary container 13 overcomes the pressure of primary liquid in primary container 11 on diaphragm 37. Thus, diaphragm 39 is biased against outlet 36 and primary liquid cannot flow through primary valve 33.

When the height of primary liquid in the sets of FIGS. 1 and 3, becomes greater than the height of the secondary liquid, the pressure of primary liquid on diaphragm 39 will then be greater than the pressure of secondary liquid, so that primary valve 33 and second primary valve 50, if present, will immediately open and allow primary liquid to flow from the primary container at the flow rate to which primary flow control 31 is adjusted. The primary flow rate is independent of the secondary flow rate. In those instances where it is less than or equal to the secondary flow rate, both primary and secondary liquid will flow through common tube 21, until air reaches air barrier 51 in the secondary flow path. Then only primary liquid will enter common tube 21. Air barrier 51 then prevents air from being drawn into common tube 21 and eventually to the patient's vein.

When primary container 11 becomes depleted of primary liquid, the primary piercing pin 23 is merely removed therefrom and inserted into the resealable closure of a new primary container, which is then suspended in place of the previous container. If primary container 11 had become empty, it will be necessary to reprime the entire system as when the first primary container was administered.

When secondary container 13 becomes depleted of secondary liquid, it can be left empty until another secondary liquid is to be administered. When another secondary liquid is to be administered, the secondary piercing pin 35 is merely removed from secondary container 13 and inserted into a new secondary liquid container. The secondary tube 19 must then be back-primed, as when the first secondary container was administered.

Having described the invention in specific detail and exemplified the manner in which it may be carried into practice, it will now be readily apparent to those skilled in the art that innumerable variations, applications, modifications and extensions of the basic principles involved may be made without departing from its sphere or scope, especially as to the choice of pilot liquid controlled primary valve to be employed.

I claim:

1. In a set for the sequential administration of medical liquids to a patient, said set including:
a primary tube for the flow of primary medical liquid therethrough and including a primary valve for controlling the flow of liquid through said primary tube, a secondary tube for the flow of a secondary medical liquid therethrough;

said primary valve being effective only to prevent the flow of primary liquid administration therethrough during administration of secondary liquid, the flow of secondary liquid through said secondary tube being independent of the operation of said primary valve, a common tube having its distal end in fluid communication with the proximal ends of said primary and secondary tube and its proximal end open for the flow of liquid therefrom to form a primary liquid flow path comprising said primary tube and said common tube and a secondary flow path comprising said secondary tube and said common tube, the improvement which comprises:

a secondary flow control means in said secondary liquid flow path for adjusting the flow rate of said secondary liquid therethrough, a primary flow control means on said primary tube for adjusting the flow rate of said primary liquid through said primary flow path to a rate independent of the flow rate of said secondary liquid through said secondary liquid flow path, and an air barrier in said secondary liquid flow path substantially impervious to air for preventing the flow of air therethrough, said primary valve characterized by a housing having an inlet thereto, an outlet therefrom, said inlet being connected in fluid communication with said primary tube for entrance of said primary liquid into and through said housing and out of said outlet, and a port not in fluid communication with said inlet and outlet to said primary valve, said port connected in fluid communication to the proximal end of a secondary liquid pilot tube which is connected in fluid communication at its distal end to said secondary tube for the flow of secondary liquid into said port, whereby said secondary liquid flowing into said port is effective to close said outlet to the flow of primary liquid from said primary valve.

2. The set defined in claim 1, wherein said primary valve is further characterized by said housing being divided into first and second chambers by an air and liquid impermeable, flexible diaphragm, said first chamber having an air vent through said housing with means associated therewith to prevent the flow of liquid therethrough and said port through said housing for liquid to enter into and exit therefrom, and said second chamber having an air vent through said housing with means associated therewith to prevent the flow of liquid therethrough, said inlet connected in fluid communication with said primary tube for the entrance of said primary liquid into said second chamber, and said outlet connected in fluid communication to said primary tube for the exit of said primary liquid from said second chamber, said outlet being opened or closed to air and liquid by movement of said diaphragm, whereby said secondary liquid entering said first chamber serves to bias said flexible diaphragm against said outlet.

3. The set defined in claim 2, wherein said outlet is normally closed by said diaphragm before said secondary liquid is present in said first chamber.

4. The set defined in claim 1 or 3, wherein said outlet is further characterized in that its inner end extends into said second chamber to form a seat on which a portion of said diaphragm seats to close said outlet.

5. The set defined in claim 4, wherein said inner end had a plurality of protrusions to form a plurality of said seats.

6. The set defined in claim 5, wherein said plurality of protrusions are concentric rings of unequal heights, the height of said rings decreasing in a direction from the perimeter of said inner end towards the center thereof.

7. The set defined in claim 2, wherein said means associated with said air vent of said second chamber is a hydrophobic membrane covering said vent.

8. The set defined in claim 2, wherein said means associated with said air vent of said first chamber is a hydrophobic membrane covering said vent.

9. The set defined in claim 2, wherein said means associated with said air vent of said first chamber is a flexible tubing having an air filter at its outer end and a flow control device thereon for controlling the flow of liquid through said tubing.

10. The set defined in claim 2, wherein said means associated with said air vent of said first chamber is a flexible tubing having an air filter at its outer end and a flow control device thereon for controlling the flow of liquid through said tubing.

11. The set defined in claim 2, wherein said inlet to said second chamber is covered at its outer end by a resealable membrane.

12. The set defined in claim 1, wherein said air barrier comprises a hydrophilic membrane disposed in a housing having an inlet and outlet in fluid communication with said secondary liquid flow path.

13. The set defined in claim 1, wherein said air barrier comprises a mechanical valve disposed in a housing having an inlet and outlet in fluid communication with said secondary tube.

14. The set defined in claim 13, wherein said mechanical valve is a float valve.

15. The set defined in claim 1 or 2, wherein said air barrier is located between the ends of said secondary tube.

16. The set defined in claim 1 or 2, wherein said air barrier is located between the ends of said common tube.

17. The set defined in claim 12 or 13, wherein said housing includes an air vent.

18. The set defined in claim 17, wherein said air vent is covered by a hydrophobic membrane.

19. The set defined in claim 1, wherein said primary tube further includes a primary piercing pin at its distal end for insertion into a container for a primary medical liquid and a drip chamber for forming drops of said primary liquid.

20. The set defined in claim 19, wherein said secondary tube further includes a secondary piercing pin at its distal end for insertion into a container for a secondary medical liquid, and a drip chamber for forming drops of secondary liquid.

21. The set defined in claim 19 or 20, wherein said piercing pins and drip chambers are integral.

22. The set defined in claim 19 or 20, wherein said peircing pins have integral air vents.

23. The set defined in claim 1 or 2, wherein said secondary flow control means is on said secondary tube.

24. The set defined in claim 1 or 2, wherein said secondary flow control means is on said common tube.

25. The set defined in claim 1, wherein said primary flow control means is on the proximal side of said primary valve and said primary tube includes a second primary valve on the proximal side of said primary flow control means further characterized as a one-way check valve that allows said primary liquid to flow towards said common tube, but prevents the flow of said secondary liquid into said primary tube.

26. The set defined in claim 1 or 2 or 25, wherein said primary tube further includes a priming tube connected thereto in fluid communication on each side of said primary flow control means and having a priming tube flow control means thereon to regulate the flow of said primary liquid through said priming tube.

27. The set defined in claim 25 and further including a chamber for a compressible mass in fluid communication with said primary tube between said primary flow control means and said second primary valve to provide a spring for relieving pressures on said second primary valve whenever the height of said primary liquid is less than the height of said secondary liquid in the system.

28. The set defined in claim 27, wherein said chamber has only one opening thereto.

29. The set defined in claim 27, wherein said chamber has an inlet and outlet in communication with said primary tube.

30. The set defined in claim 27, wherein said compressible mass is air.

* * * * *